United States Patent
Yoon et al.

(10) Patent No.: US 10,607,820 B2
(45) Date of Patent: Mar. 31, 2020

(54) MONITORING UNITS, PLASMA TREATMENT DEVICES INCLUDING THE SAME, AND METHODS OF FABRICATING SEMICONDUCTOR DEVICES USING THE SAME

(71) Applicant: Samsung Electronics Co., Ltd., Suwon-si, Gyeonggi-do (KR)

(72) Inventors: Junho Yoon, Suwon-si (KR); Jaehyun Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 6 days.

(21) Appl. No.: 15/400,126

(22) Filed: Jan. 6, 2017

(65) Prior Publication Data
US 2018/0090303 A1  Mar. 29, 2018

(30) Foreign Application Priority Data

Sep. 27, 2016  (KR) .......................... 10-2016-0123919

(51) Int. Cl.
| | | |
|---|---|---|
| *H01L 21/00* | (2006.01) | |
| *H01J 37/32* | (2006.01) | |
| *G01N 29/12* | (2006.01) | |
| *G01N 29/24* | (2006.01) | |
| *H01L 21/3065* | (2006.01) | |
| *H01L 21/66* | (2006.01) | |

(52) U.S. Cl.
CPC ........ *H01J 37/32935* (2013.01); *G01N 29/12* (2013.01); *G01N 29/2437* (2013.01); *H01J 37/3299* (2013.01); *H01J 37/32568* (2013.01); *H01L 21/3065* (2013.01); *H01L 22/14* (2013.01); *H01L 22/20* (2013.01); *H01J 2237/334* (2013.01)

(58) Field of Classification Search
None
See application file for complete search history.

(56) References Cited

U.S. PATENT DOCUMENTS

| | | | | |
|---|---|---|---|---|
| 5,569,502 A | * | 10/1996 | Koinuma | ................ C23C 16/24 427/248.1 |
| 6,458,239 B1 | * | 10/2002 | Bhardwaj | ............. H01J 37/321 118/712 |
| 6,902,646 B2 | * | 6/2005 | Mahoney | .......... H01J 37/32935 118/712 |

(Continued)

FOREIGN PATENT DOCUMENTS

| | | |
|---|---|---|
| JP | 2005-228727 | 8/2005 |
| KR | 1020070095241 A | 9/2007 |
| KR | 1020140101671 | 8/2014 |

*Primary Examiner* — Parviz Hassanzadeh
*Assistant Examiner* — Michelle Crowell
(74) *Attorney, Agent, or Firm* — Sughrue Mion, PLLC

(57) ABSTRACT

A monitoring unit for monitoring a plasma process chamber includes a piezoelectric member comprising a surface that is exposed within the plasma process chamber, a first electrode coupled to the piezoelectric member, a power supply unit coupled to the first electrode and configured to apply a voltage to the piezoelectric member through the first electrode, and a control unit coupled to the piezoelectric member and configured to detect a vibration frequency of the piezoelectric member. The vibration frequency is generated in response to the voltage applied to the piezoelectric member.

16 Claims, 11 Drawing Sheets

(56) References Cited

U.S. PATENT DOCUMENTS

| | | | |
|---|---|---|---|
| 2002/0179245 A1 | 12/2002 | Masuda et al. | |
| 2004/0011379 A1* | 1/2004 | Anaokar | B08B 7/00 |
| | | | 134/1.1 |
| 2004/0125360 A1* | 7/2004 | Ludviksson | G01N 21/645 |
| | | | 356/72 |
| 2004/0214435 A1* | 10/2004 | Yuasa | H01J 37/32935 |
| | | | 438/689 |
| 2005/0092239 A1* | 5/2005 | Grimshaw | C23C 14/546 |
| | | | 118/712 |
| 2005/0213079 A1* | 9/2005 | Fink | G01N 21/73 |
| | | | 356/72 |
| 2006/0100824 A1* | 5/2006 | Moriya | H01J 37/32935 |
| | | | 702/183 |
| 2009/0108382 A1* | 4/2009 | Eriksen | C23C 14/021 |
| | | | 257/419 |
| 2010/0151599 A1* | 6/2010 | Bai | H01L 22/12 |
| | | | 438/17 |
| 2012/0247667 A1 | 10/2012 | Hashiguchi et al. | |
| 2013/0228550 A1 | 9/2013 | Mori et al. | |
| 2014/0127833 A1* | 5/2014 | Kim | C23C 16/52 |
| | | | 438/5 |
| 2015/0194292 A1 | 7/2015 | Kaneko et al. | |
| 2015/0381149 A1 | 12/2015 | Iwabuchi | |
| 2017/0133283 A1* | 5/2017 | Kenworthy | G05B 15/02 |
| 2018/0052104 A1* | 2/2018 | Larsson | H01J 37/32467 |

\* cited by examiner

MONITORING UNITS, PLASMA TREATMENT DEVICES INCLUDING THE SAME, AND METHODS OF FABRICATING SEMICONDUCTOR DEVICES USING THE SAME

CROSS-REFERENCE TO RELATED APPLICATION

This application claims priority to and the benefit of Korean Patent Application No. 10-2016-0123919 filed in the Korean Intellectual Property Office on Sep. 27, 2016, the disclosure of which is hereby incorporated herein by reference.

BACKGROUND

The present disclosure relates to semiconductor processing equipment, and in particular to monitoring unit for monitoring the operation of a plasma treatment apparatus.

Semiconductor fabrication processes include deposition processes for forming thin films on a semiconductor wafer (hereinafter, referred to as a "substrate"), etching processes for selectively removing material from the substrate, and the like. Many semiconductor fabrication processes involve a treatment using plasma. A semiconductor fabrication process using a plasma is referred to herein as a "plasma treatment process," and can include a plasma deposition process, a plasma etching process, a plasma cleaning process, and the like. The use of a plasma treatment process may decrease the amount of time needed to perform a semiconductor fabricating process, and/or may allow the process to be more easily controlled, so that it may be possible to perform a more precise operation.

In a plasma etching process, the plasma is used to selectively remove a thin film from a substrate. The plasma is created by supplying a reaction gas into a chamber in which the substrate is placed, and applying radio frequency (RF) electromagnetic energy to the reaction gas to generate the plasma. The RF energy is applied to an upper and lower electrode that are disposed within the chamber. In order to improve treatment efficiency, a ring-shaped insulating member may be disposed around the upper electrode and/or the lower electrode, and plasma is formed above an upper portion of the substrate. The ring-shaped insulating member is typically formed from quartz.

During a plasma process, some components of the etching apparatus are exposed to the plasma within the chamber. In particular, the ring-shaped insulating members are exposed to the plasma during the plasma process. The plasma, which has a high energy, can cause exposed components within the chamber to erode. In particular, quartz components within the chamber are susceptible to erosion. When the quartz ring-shaped insulating members erode, process conditions within the chamber can change. Thus, it is generally advisable to replace the ring-shaped insulating members from time to time before they erode to the point that a process defect is generated.

If a plasma process, such as a plasma etching process, is not terminated at an appropriate time, the quality of the device that is being fabricated may be degraded. Moreover, particles from the eroded component of the apparatus may contaminate the device. An etching defect may be generated due to a difference in a process condition, such as temperature, etching speed, and the like. When a ring-shaped insulating member erodes, process conditions may vary across the surface of the substrate. Thus, for example, an edge portion of the substrate may have a higher risk of being damaged than a center of the substrate.

In general, an etching process may be monitored using optical emission spectroscopy (OES). OES is a method that detects a change in an optical characteristic of the plasma. OES has a problem, however, in that the sensitivity of OES may degrade over time, and/or it may be difficult to spatially monitor a plasma process using OES.

The above information disclosed in this Background section is only for enhancement of understanding of the background of the invention and therefore it may contain information that does not form the prior art that is already known in this country to a person of ordinary skill in the art.

SUMMARY

Some embodiments provide a monitoring unit that is capable of monitoring a plasma treatment process by using a vibrator formed of a piezoelectric member.

Some further embodiments provide a monitoring unit that is capable of monitoring a plasma treatment process using a quartz component within a plasma treatment chamber.

Some further embodiments provide a method of fabricating a semiconductor device that includes monitoring a characteristic of a quartz component that is disposed within a plasma treatment chamber.

A monitoring unit for monitoring a plasma process chamber according to some embodiments includes a piezoelectric member comprising a surface that is exposed within the plasma process chamber, a first electrode coupled to the piezoelectric member, a power supply unit coupled to the first electrode and configured to apply a voltage to the piezoelectric member through the first electrode, and a control unit (controller) coupled to the piezoelectric member and configured to detect a vibration frequency of the piezoelectric member. The vibration frequency is generated in response to the voltage applied to the piezoelectric member.

A method of forming a semiconductor device according to some embodiments includes providing a substrate in a plasma process chamber, providing a piezoelectric member within the plasma process chamber, performing a plasma treatment process on the substrate in the plasma process chamber, and detecting a change in a piezoelectric property of the piezoelectric member in response to the plasma treatment process.

A plasma treatment apparatus according to some embodiments includes a chamber, a stage in the chamber, wherein the stage is configured to support a substrate that is to be subjected to a plasma treatment process, a head plate in the chamber and disposed to face the stage, and a monitoring unit configured to monitor the plasma treatment process within the chamber. The monitoring unit includes a piezoelectric member having a surface that is exposed within the chamber, a pair of electrodes connected to a power supply unit and configured to apply a voltage to the piezoelectric member, and a control unit (controller) configured to detect a change in a vibration frequency of the piezoelectric member. The vibration frequency is generated in response to the voltage applied to the piezoelectric member.

DETAILED DESCRIPTION OF THE EMBODIMENTS

Hereinafter, a monitoring unit according to an exemplary embodiment of the present closure will be described with reference to the drawings. Some embodiments provide an apparatus and/or method that is capable of monitoring, in real time, the degree of erosion of a component within a plasma treatment chamber, so that the component can be replaced before the erosion becomes to great.

Figure 1A:
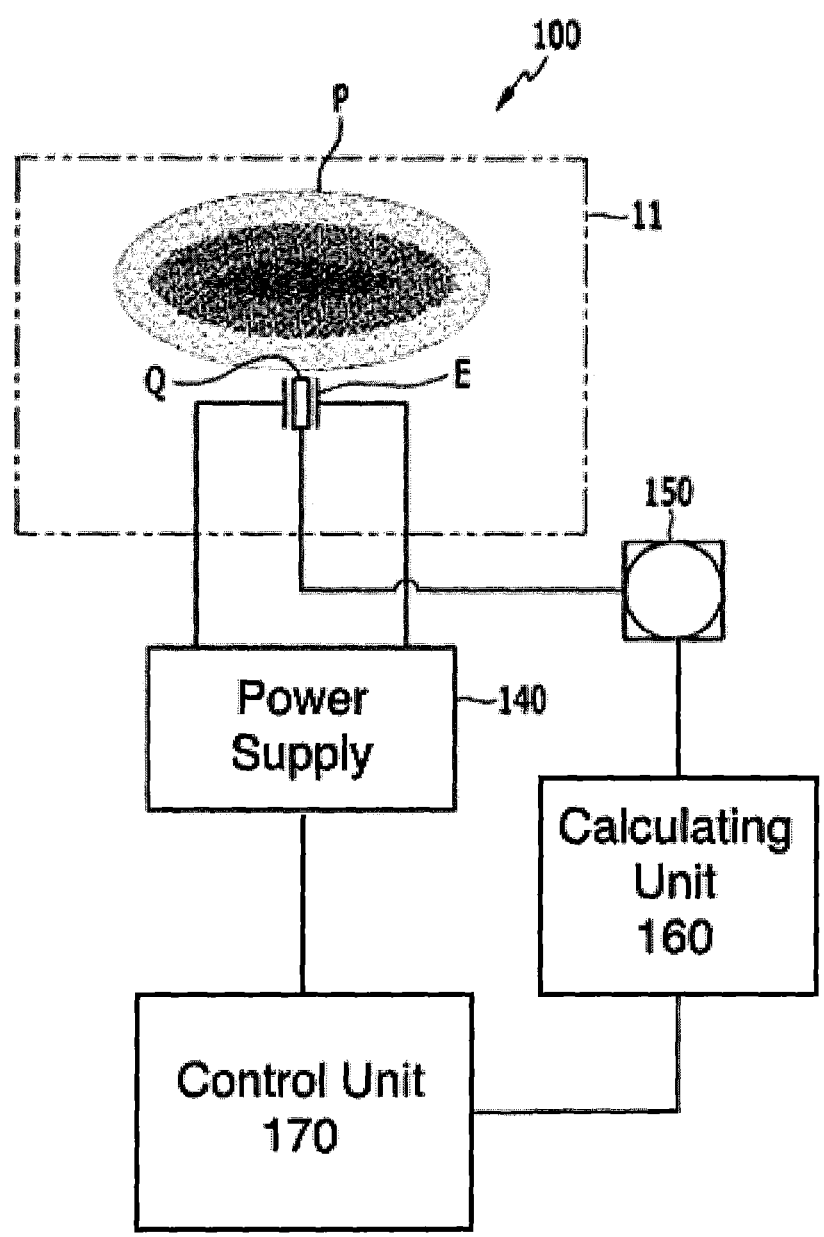
FIG. 1A is a diagram schematically illustrating a monitoring unit according to some embodiments.

FIG. 1A is a diagram schematically illustrating a monitoring unit according to some embodiments.

Referring to FIG. 1A, a monitoring unit 100 is provided within a chamber 11 in which a process (hereinafter, a plasma treatment process) using plasma P is performed. The chamber 11 may be referred to as a "process chamber," a "plasma treatment chamber," and/or a "reaction chamber." The monitoring unit 100 includes a piezoelectric member Q, a pair of electrodes E, a power supply unit 140 connected to the electrodes E and configured to apply a voltage to the pair of electrodes E, and an RF sensing unit 150 that senses a frequency of vibration of the piezoelectric member Q. The piezoelectric member Q may be disposed between the pair of electrodes E. The monitoring unit 100 further includes a calculating unit 160 that detects a change in the frequency of vibration of the piezoelectric member Q, and a control unit 170 connected to the calculating unit 160 and the power supply 140. The control unit 170 controls a frequency and/or a magnitude of a voltage applied to the electrodes E.

The piezoelectric member Q is a member which is mechanically transformed when a voltage is applied, and may be, for example, a member that generates a mechanical and/or electrical vibration when a voltage is applied thereto. In some embodiments, the piezoelectric member Q may be formed of a quartz crystal, which has a piezoelectric property such that when a voltage is applied to the quartz crystal, a vibration of a uniform frequency is generated. The piezoelectric member Q is not limited to the quartz, but may include other piezoelectric materials. For convenience of description, only a quartz piezoelectric member Q will be described herein.

The pair of electrodes E are disposed with the piezoelectric member Q interposed therebetween for the purpose of applying a voltage to the piezoelectric member Q. The electrodes E receive a voltage generated by power supply unit 140, which may be an external power supply unit. That is, when a voltage is applied to the piezoelectric member Q through the electrodes E, a vibration is generated in the piezoelectric member Q due to the piezoelectric effect.

Figure 1B:
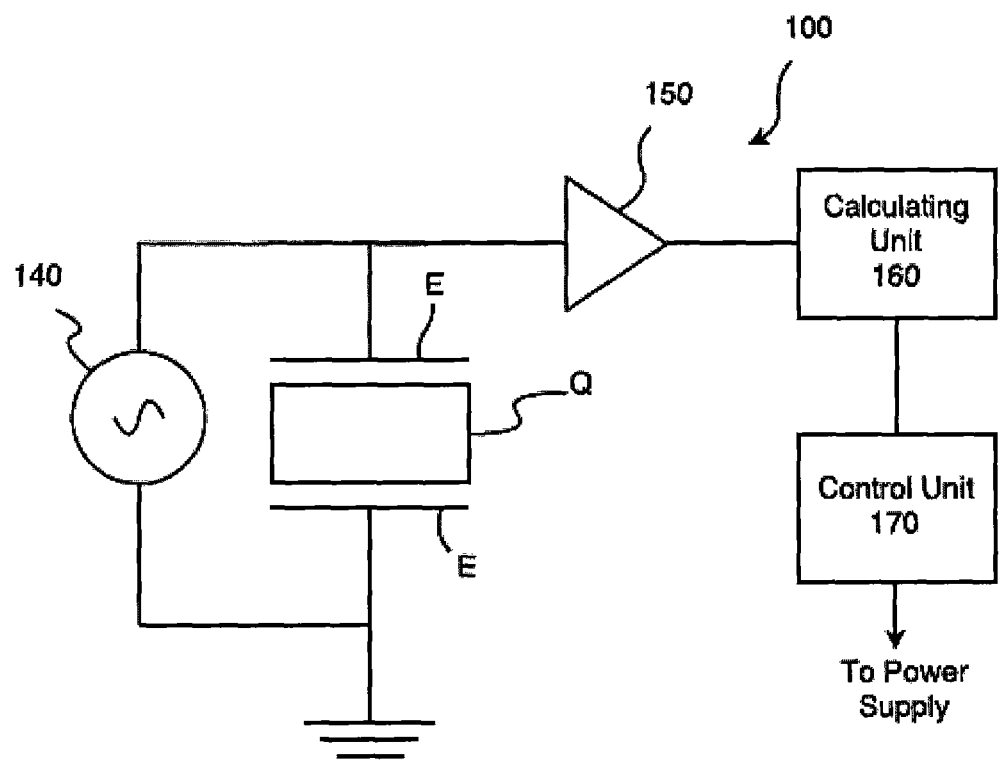
FIG. 1B is a schematic circuit diagram that illustrates a circuit for monitoring erosion of a component of a plasma treatment chamber according to some embodiments.

FIG. 1B is a circuit diagram illustrating an arrangement of the monitoring unit 100. Referring to FIG. 1B, the power supply 140 applies a DC or AC voltage to the electrodes E on the piezoelectric member Q. An electrode E is connected to the RF sensing unit 150, which may include an amplifier that senses and amplifies a frequency of vibration of the piezoelectric member Q. The sensed frequency is provided to the calculating unit 160, which measures changes in the sensed frequency.

As described above, the combination of the piezoelectric member Q and the pair of electrodes E may provide a vibrator, or resonating element. For example, when the pair of electrodes E is provided on opposite sides of a plate-shaped piezoelectric member Q formed of quartz, the piezoelectric member Q may serve as a vibrator. Accordingly, when a voltage is applied to the piezoelectric member Q through the electrodes E, a vibration of a uniform frequency may be generated in the piezoelectric member Q. The frequency of vibration of the piezoelectric member E is influenced by a thickness or a mass of the piezoelectric member Q, so that when the piezoelectric member Q becomes thinner, the frequency is increased.

Referring again to FIG. 1A, the piezoelectric member Q, which is positioned within the chamber 11, is exposed to the plasma P, so that a surface of the piezoelectric member Q may become eroded by an influence of the plasma P and/or a gas used in the process while the plasma treatment process is being performed. Alternatively or additionally, deposits may become attached to the surface of the piezoelectric member Q during the plasma treatment process. Accordingly, when a change in a frequency of vibration generated in response to a voltage being applied to the piezoelectric member Q is analyzed, it is possible to detect an amount of corrosion of the piezoelectric member Q and/or a degree of the attachment of the deposits. Thus a monitoring unit 100 according to some embodiments may monitor various characteristics within the plasma treatment apparatus by using a property that a vibration frequency of a piezoelectric member changes when a thickness or a mass of the piezoelectric member changes. A plasma treatment process and/or the condition of a plasma treatment chamber may be monitored or controlled using a monitoring unit 100 according to various embodiments described herein. That is, a condition of equipment within a plasma treatment chamber in which the process is performed and/or a progress of a plasma treatment process itself may be monitored and/or controlled according to various embodiments described herein.

For convenience of description, the embodiments described herein will be described primarily with reference to a plasma etching process. However, the inventive concepts are not limited to an etching process, and may also be applied to any other plasma treatment processes.

Figure 2:
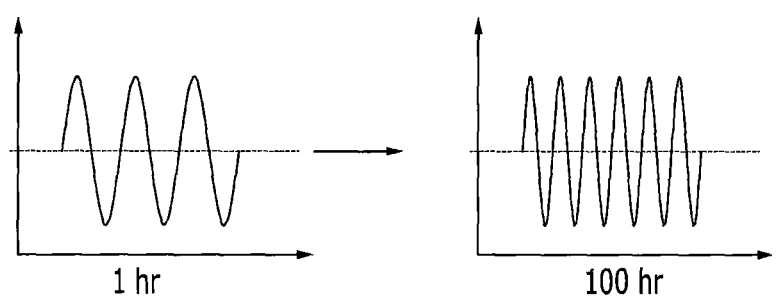
FIG. 2 is a diagram for describing a frequency change measured by the monitoring unit of FIG. 1.

FIG. 2 is a diagram illustrating a change in a frequency of vibration measured by the monitoring unit 100 of FIGS. 1A and 1B.

Referring to FIG. 2, the graph on the left-hand side represents a frequency of vibration of the piezoelectric member Q of the monitoring unit 100 after one hour of an etching process, and the graph on the right-hand side represents a frequency of the piezoelectric member Q of the monitoring unit 100 after 100 hours of the etching process. A surface of the piezoelectric member Q of the monitoring unit 100 may become eroded due to operation of the etching process. As can be seen by comparing the two graphs in FIG.

1, the frequency of the vibration increases over time. As a result, it is possible for the calculating unit 160 to measure a degree of erosion of the piezoelectric member Q by monitoring a frequency of vibration of the piezoelectric member Q in real time.

Referring again to FIG. 1B, the piezoelectric member Q is connected to the sensing unit 150, which is in turn connected to the calculating unit 160. The sensing unit 150 detects vibration of the piezoelectric member A, and the calculating unit 160 measures the frequency of vibration. Further, the power supply unit 140 is connected to the pair of electrodes E and applies a voltage to the piezoelectric member Q that is selected to cause the piezoelectric member Q to oscillate.

Hereinafter, various exemplary embodiments of a plasma treatment apparatus including the monitoring unit 100 will be described in detail with reference to different drawings.

Figure 3:
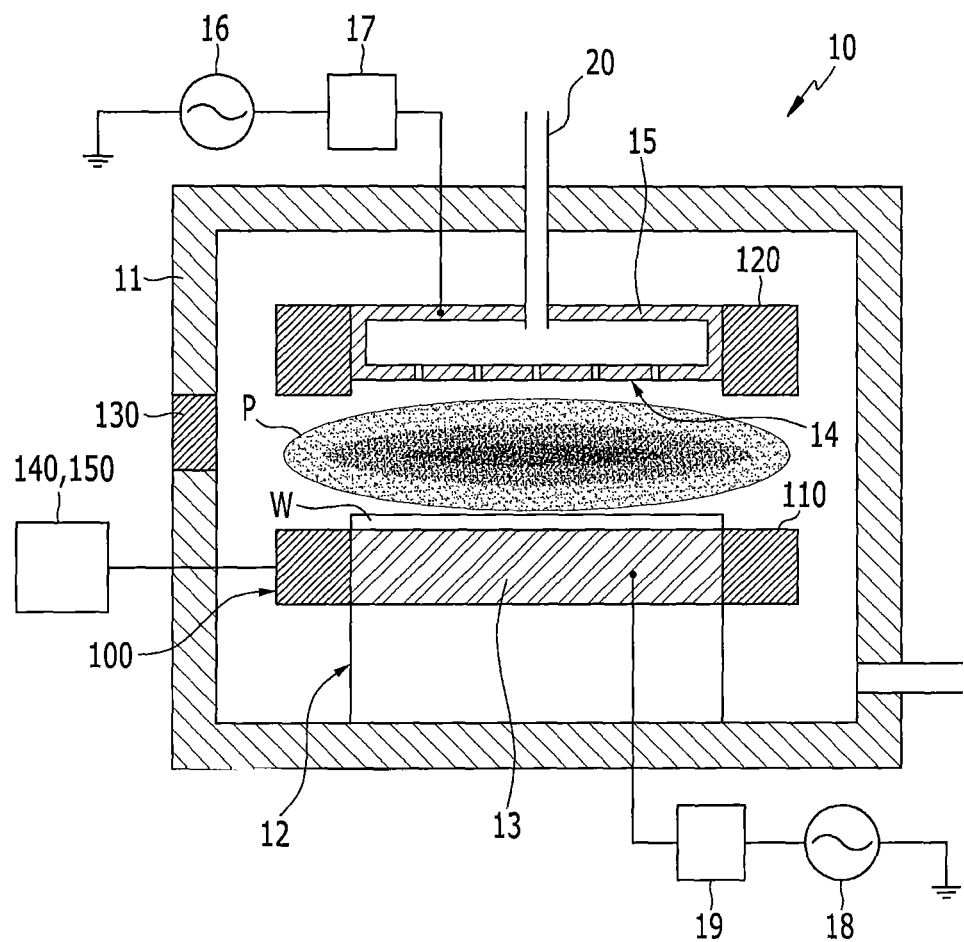
FIG. 3 is a schematic cross-sectional view of a plasma treatment apparatus according to some embodiments.

FIG. 3 is a schematic cross-sectional view of a plasma treatment apparatus according to some embodiments.

The description below is based on a case in which a plasma treatment apparatus 10 is a plasma etching apparatus.

Referring to FIG. 3, the plasma treatment apparatus 10 includes a chamber 11, a head plate 14, a stage 12, and a monitoring unit 100.

The chamber 11 defines a space in which a plasma treatment process is performed on a substrate W. The substrate W represents a material to be treated. The chamber 11 may be sealed from the outside and maintain a vacuum state. The chamber 11 may be connected with a discharge line for discharging gas at one side of a lower portion thereof, and the discharge line may be connected to a vacuum pump (not illustrated). The chamber 11 may have a cylindrical shape or any other appropriate shape.

The head plate 14 is configured for providing a reaction gas that is used to form a plasma within the chamber 11. The head plate 14 may be disposed in an upper space of the chamber 11. Further, for an effective plasma reaction, the head plate 14 may be disposed to face a stage 12 (described below) on which the substrate W is placed. Further, the head plate 14 may include a head electrode 15 to which radio frequency (RF) power is applied. The RF power may be generated by a power supply 16. Accordingly, the reaction gas supplied from the head plate 14 onto the substrate W may become plasma due to a voltage applied to the head electrode 15. The power supply 16 may be connected to the head electrode 15 via a filter 17, so that it is possible to apply a voltage within a predetermined range to the head electrode 15. The filter 17 may also reduce/prevent RF energy applied to a stage electrode 13 from interfering with the RF power applied to the head electrode 15.

The stage 12, which supports the substrate W, may be disposed in a lower space of the chamber 11, and may be disposed so as to face the head plate 14 so that the substrate W is disposed adjacent the head plate 14. Although not illustrated in the drawing, the stage 12 may include a means, such as an electrostatic chuck (not illustrated), for adsorbing and supporting the substrate W. Further, the stage 12 may include a stage electrode 13, to which RF energy is applied from an RF bias power source 18. In some embodiments, the stage electrode 13 may be biased with a DC bias. Accordingly, it is possible to attract ions from the plasma P onto the substrate W and to control the energy of the ions. In the meantime, the stage electrode 13 is connected to a filter 19, so that it is possible to apply a required voltage having a frequency within a predetermined range to the stage electrode 13 while reducing/preventing the RF component applied to the head electrode 15 from intruding.

According to the embodiments illustrated in FIG. 3, a piezoelectric member Q (see FIG. 1) of the monitoring unit 100 may be formed in a ring shape, and may be disposed at a position corresponding to a border of the substrate W. Accordingly, the monitoring unit 100 may monitor a characteristic of the plasma treatment process, for example, an etching process, at the border of the substrate W.

Referring to FIG. 3, the monitoring unit 100 may include a first quartz ring 110. The first quartz ring 110 may be formed of quartz, and may be disposed around the stage 12 adjacent an outer border of the substrate W. For example, the first quartz ring 110 may include a cover ring that protects the stage 12 from being damaged during the etching process of the substrate W. In this case, the cover ring may be formed of quartz. The first quartz ring 110 may further include a focus ring for storing the plasma P near an upper side of the substrate W and increasing a density of the plasma. In this case, the focus ring may be formed of quartz.

As described above, a piezoelectric member Q (see FIG. 1) of the monitoring unit 100 may be provided by the first quartz ring 110 that is disposed around the border of the substrate W on the stage 12. A pair of electrodes may be disposed within the first quartz ring 110, so that the first quartz ring 110 may provide a vibrator that vibrates at a uniform frequency in response to an applied voltage. Hereinafter, various forms in which the first quartz ring 110 may be configured will be described with reference to the drawing.

Figure 4:
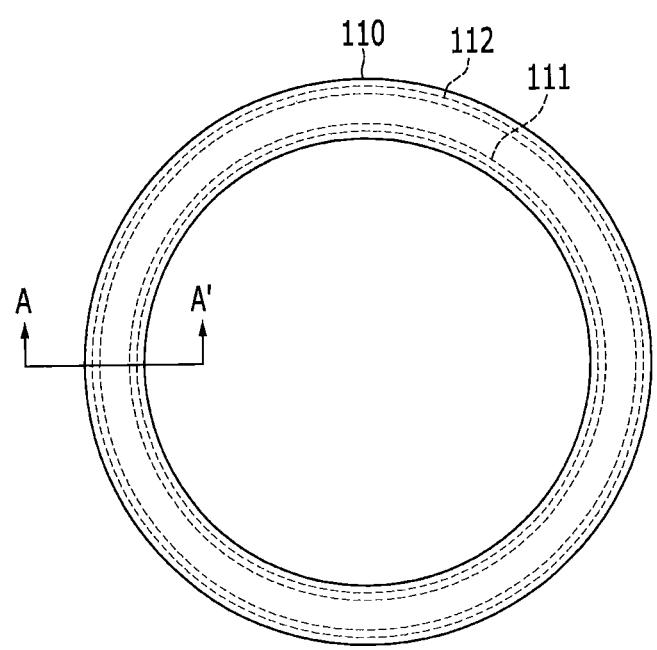
FIG. 4 is a top plan view illustrating a vibrator in a monitoring unit in the plasma treatment apparatus of FIG. 3.
Figure 5:
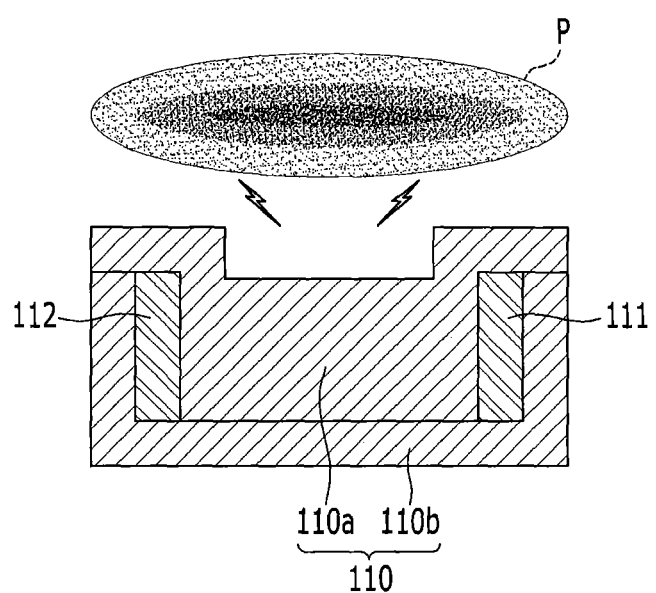
FIG. 5 is a cross-sectional view in direction A-A' of FIG. 4.

FIG. 4 is a top plan view illustrating the vibrator in the monitoring unit 100 in the plasma treatment apparatus of FIG. 3, and FIG. 5 is a cross-sectional view in direction A-A' of FIG. 4.

As shown therein, at least one of the pair of electrodes configuring the vibrator may be inserted into and installed inside the piezoelectric member Q (see FIG. 1) so as not to be exposed to the plasma. Accordingly, it is possible to reduce/prevent the plasma from being influenced due to an exposed electrode and thereby reduce/prevent the process from being influenced.

Referring to FIG. 4, an electrode may be inserted into and disposed within each of an inner peripheral portion and an outer peripheral portion of the first quartz ring 110. That is, both the pair of electrodes 111 and 112 may be inserted into and installed inside the first quartz ring 110. The pair of electrodes 111 and 112 may be formed in ring shapes. Accordingly, the first quartz ring 110, into which the pair of electrodes 111 and 112 are inserted, may serve as a vibrator, so that when a voltage is applied to the first quartz ring 100 through the pair of electrodes 111 and 112, the first quartz ring 110 vibrates at a uniform frequency.

Referring to FIG. 5, in a case of the etching process, a portion of the first quartz ring 110 positioned between the pair of electrodes 111 and 112 in the first quartz ring 110 may be exposed to and eroded by the plasma P. Thus, as the etching process progresses, a thickness of the portion of the first quartz ring 110 positioned between the pair of electrodes 111 and 112 is decreased, which changes a frequency at which the first quartz ring 110 vibrates. Otherwise, even though the first quartz ring 110 is not directly exposed to the plasma P, the first quartz ring 110 may be slightly consumed by various factors during to the progress of the plasma treatment process, so that a frequency at which the first quartz ring 110 vibrates may also change. Although not illustrated in the drawing, in the case of a deposition process, material may be deposited in the portion positioned between the pair of electrodes 111 and 112 in the first quartz ring 110, so that as the deposition process progresses, a thickness of the portion positioned between the pair of electrodes 111 and 112 in the first quartz ring 110 increased, which also causes the frequency at which the first quartz ring 110 vibrates to change.

In order to facilitate insertion of the pair of electrodes 111 and 112 into the first quartz ring 110, the first quartz ring 110 may be divided into a plurality of pieces. FIG. 5 is an example in which the first quartz ring 110 is manufactured by dividing the first quartz ring 110 into two pieces 110a and 110b in order to facilitate insertion of the pair of electrodes 111 and 112 into the inner peripheral portion and the outer peripheral portion of the first quartz ring 110. The vibrator may be manufactured by inserting the pair of electrodes 111 and 112 into the first quartz ring 110, which is manufactured with the two divided pieces 110a and 110b, and then bonding the two pieces 110a and 110b. The bonding of the two pieces 110a and 110b may use any suitable fastening means, such as an adhesive and/or a bolt. The fastening means may be formed of a material that does not have reactivity to plasma. Further, the two pieces 110a and 110b may be bonded so that a clearance is not generated between the divided pieces.

Figure 6:
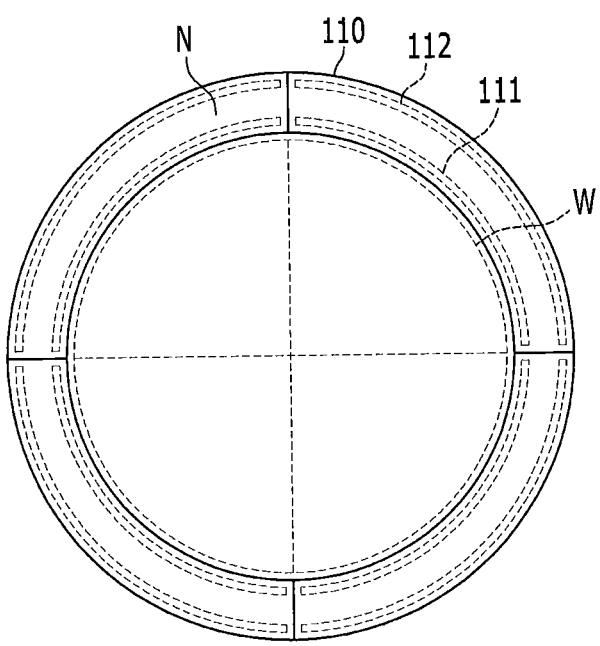
FIG. 6 is a diagram illustrating a modified example of the vibrator in the monitoring unit in the plasma treatment apparatus of FIG. 3.

FIG. 6 is a is a top plan diagram illustrating a modified example of the vibrator in the monitoring unit in the plasma treatment apparatus of FIG. 3.

In the embodiment of FIG. 6, a piezoelectric member Q may be radially divided into a plurality of arc-shaped elements N along a circumference of the piezoelectric member Q. By dividing the piezoelectric member Q into a plurality of circumferential pieces or elements, it is possible to monitor a spatial uniformity of a plasma treatment process.

Referring to FIG. 6, the first quartz ring 110 may be formed of a plurality of radially divided pieces N. For example, the first quartz ring 110 may be formed of four pieces N, and a pair of electrodes 111 and 112 may be inserted into and installed in an inner peripheral surface and an outer peripheral surface in each of the four divided pieces N. In this case, a voltage may be applied to each of the pair of electrodes provided within each of the divided pieces N. Further, the plurality of divided pieces N may be arranged so as not to be spaced apart from each other, so that they do not adversely affect the functionality of the first quartz ring 110. FIG. 6 illustrates a case in which the vibrator formed of the first quartz ring 110 and the pair of electrodes 111 and 112 is divided into four pieces as an example, but the present disclosure is not limited thereto, and the vibrator may, for example, be into three or less pieces or five or more pieces.

Because the first quartz ring 110 is radially divided, it is possible to easily monitor whether the etching process is spatially uniform. Referring to FIG. 6, the first quartz ring 110 is disposed along a border of the substrate W, so that when the first quartz ring 110 is divided into four pieces N, it is possible to detect whether the etching process is evenly performed on a section of the substrate W corresponding to each piece.

For example, when a difference of a frequency of vibration between the four pieces N according to the progress of the etching process is within a reference range, it may be determined that the etching process is uniform in an upper space corresponding to the four pieces N. In contrast, when the difference in the frequency of vibration between the four pieces N is outside the reference range, it may be determined that the etching process is not uniform in the upper space corresponding to the four pieces N. Moreover, it may be possible to detect a section of the quartz ring 110 that is more heavily etched, and a section that is less heavily etched by comparing the frequencies of the respective pieces.

Figure 7:
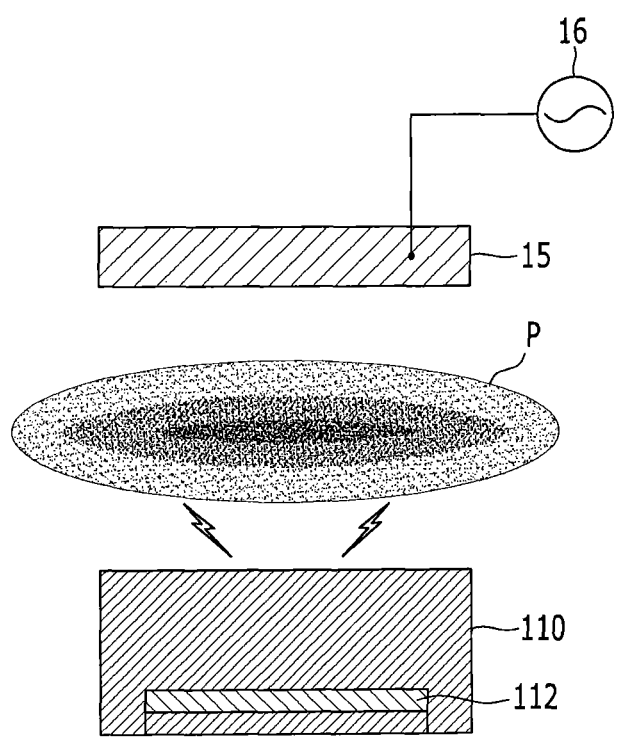
FIG. 7 is a diagram illustrating another modified example of the vibrator in the monitoring unit in the plasma treatment apparatus of FIG. 3.

FIG. 7 is a diagram illustrating in cross-section a vibrator in a monitoring unit in the plasma treatment apparatus of FIG. 3 according to further embodiments.

As shown therein, one electrode in the pair of electrodes in a vibrator of the monitoring unit 100 may be provided by an electrode for generating plasma within the chamber 11. Accordingly, an electrode provided in an existing plasma etching apparatus may be used as an electrode of the vibrator of the monitoring unit 100.

Referring to FIG. 7, one electrode 112 in the pair of electrodes of the vibrator may be inserted into and installed in the first quartz ring 110, and the other electrode may be a head electrode 15 of a head plate 14 (see FIG. 3) to which an RF voltage is applied for generating plasma P. For example, one electrode, that is, the head electrode 15, may be disposed above the first quartz ring 110 with the plasma P interposed therebetween, and the other electrode may be inserted into and installed in a lower portion of the first quartz ring 110. Accordingly, when a voltage is applied to the head electrode 15, a current may be transmitted to the first quartz ring 110 through the plasma P that is a conductor, and may flow to the other electrode 112 disposed to face the head electrode 15 inside the first quartz ring 110. An upper portion of the first quartz ring 110 is exposed to the plasma P is eroded during the plasma treatment process. When the upper portion of the first quartz ring is eroded, a frequency of the vibrator changes. In this embodiment, only one electrode is provided within the first quartz ring 110, and the head electrode 15 of the plasma etching apparatus may be used as an electrode of the vibrator. In this embodiment, it may not be necessary to provide a separate voltage supply means, for example, the voltage supply unit 140 (see FIG. 1), to supply a voltage to the vibrator.

Although not illustrated, even in a case of the form illustrated in FIG. 7, the vibrator may be radially divided into a plurality of circumferential pieces. In that case, the electrode 112 that is inserted into the first quartz ring 110 may also be divided into a plurality of pieces. However, the head electrode 15 may be a common electrode for the vibrator of each of the plurality of pieces. The related matters are not repeatedly described, and the aforementioned contents may be applied thereto as they are.

Figure 8:
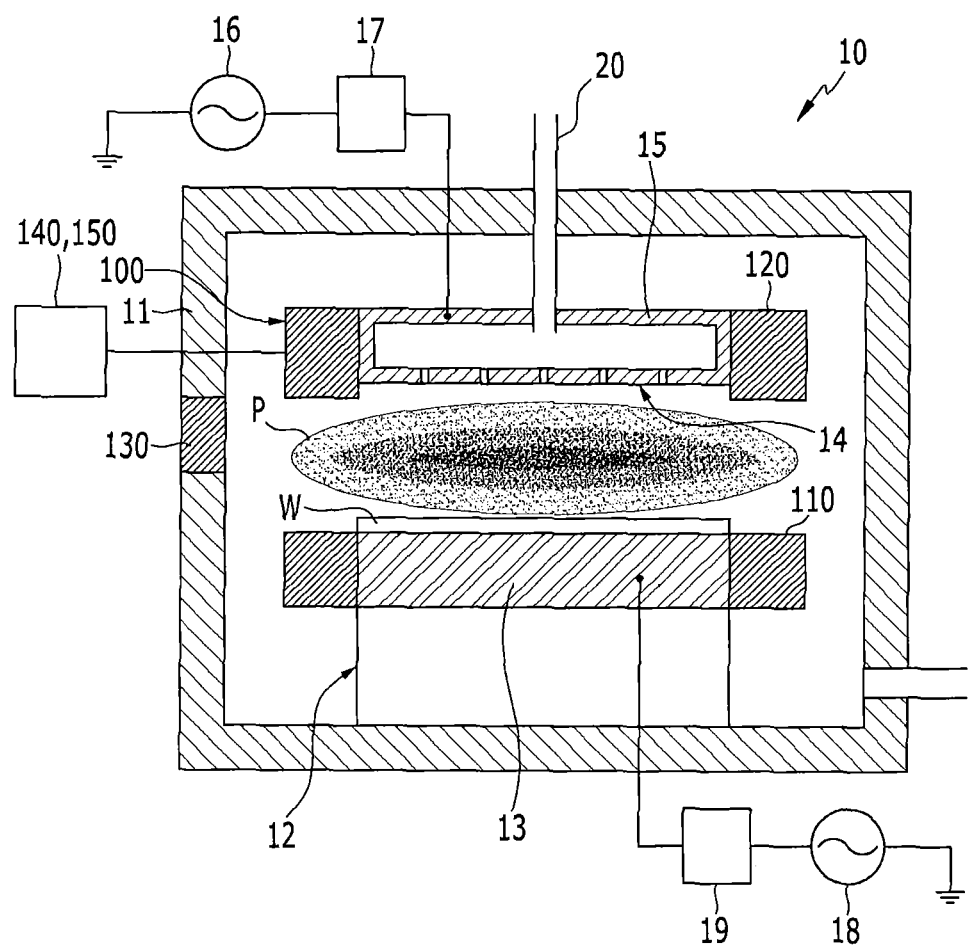
FIG. 8 is a schematic cross-sectional view of a plasma treatment apparatus according to further embodiments.

FIG. 8 is a schematic cross-sectional view of a plasma treatment apparatus according to a second exemplary embodiment. In the following description, only differences with previously disclosed embodiments will be described, and a description of like elements will be omitted.

Referring to FIG. 8, a monitoring unit 100 includes a second quartz ring 120. The second quartz ring 120 may be formed of quartz, and may be disposed around a periphery of a head plate 14. For example, the second quartz ring 120 may include a shield ring for storing plasma P in an upper side of a substrate W and increasing a density of plasma. In this case, the shield ring may be formed of quartz.

As described above, a piezoelectric member Q (see FIG. 1) of the monitoring unit 100 may be formed of the second quartz ring 120 disposed around the border of the head plate 14, and a pair of electrodes may be disposed with the second quartz ring 120 interposed therebetween, so that the piezoelectric member Q may provide a vibrator vibrating at a uniform frequency. In some embodiments, the pair of electrodes configuring the vibrator may be inserted into and installed in an inner peripheral portion and an outer peripheral portion of the second quartz ring 120. In other embodiments, one of the pair of electrodes configuring the vibrator may be inserted into and installed in an upper portion of the second quartz ring 120, and the other of the pair of electrodes configuring the vibrator may be provided by the stage electrode 13, which is included in the stage 12. In some embodiments, the second quartz ring 120 and/or the electrode(s) disposed therein may be formed of a plurality of divided pieces as described above.

Figure 9:
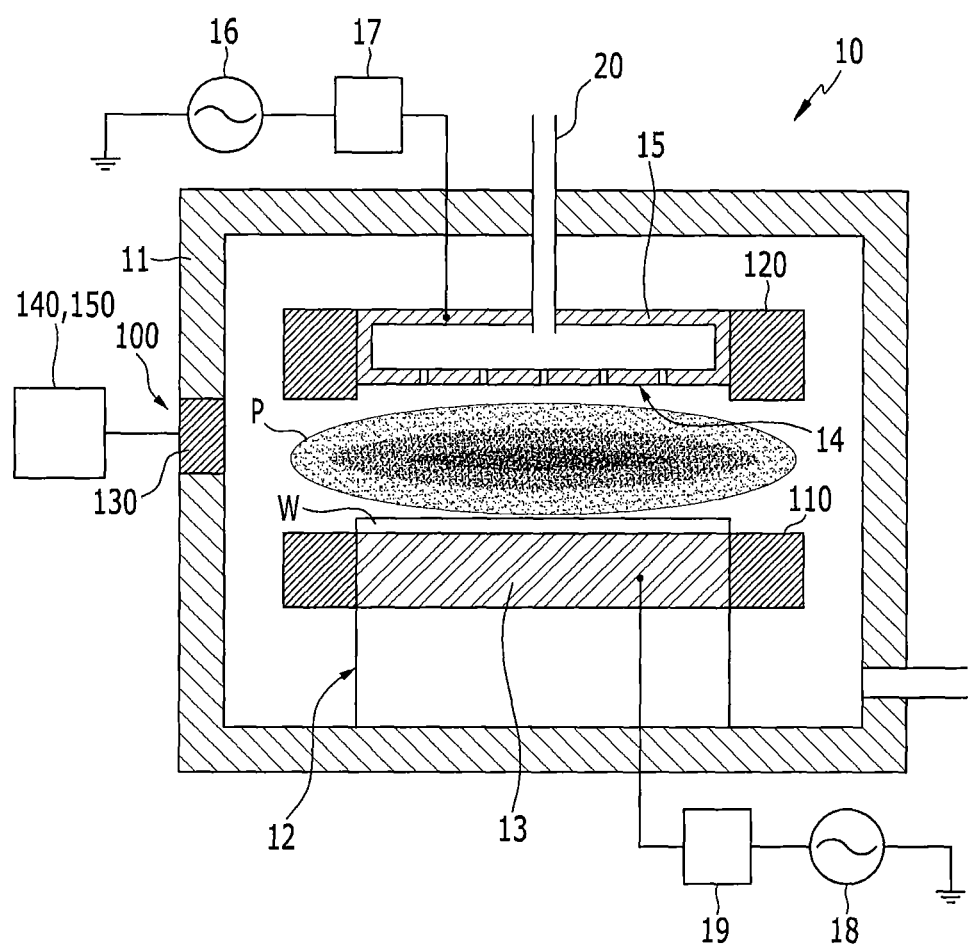
FIG. 9 is a schematic cross-sectional view of a plasma treatment apparatus according to further embodiments.
Figure 10:
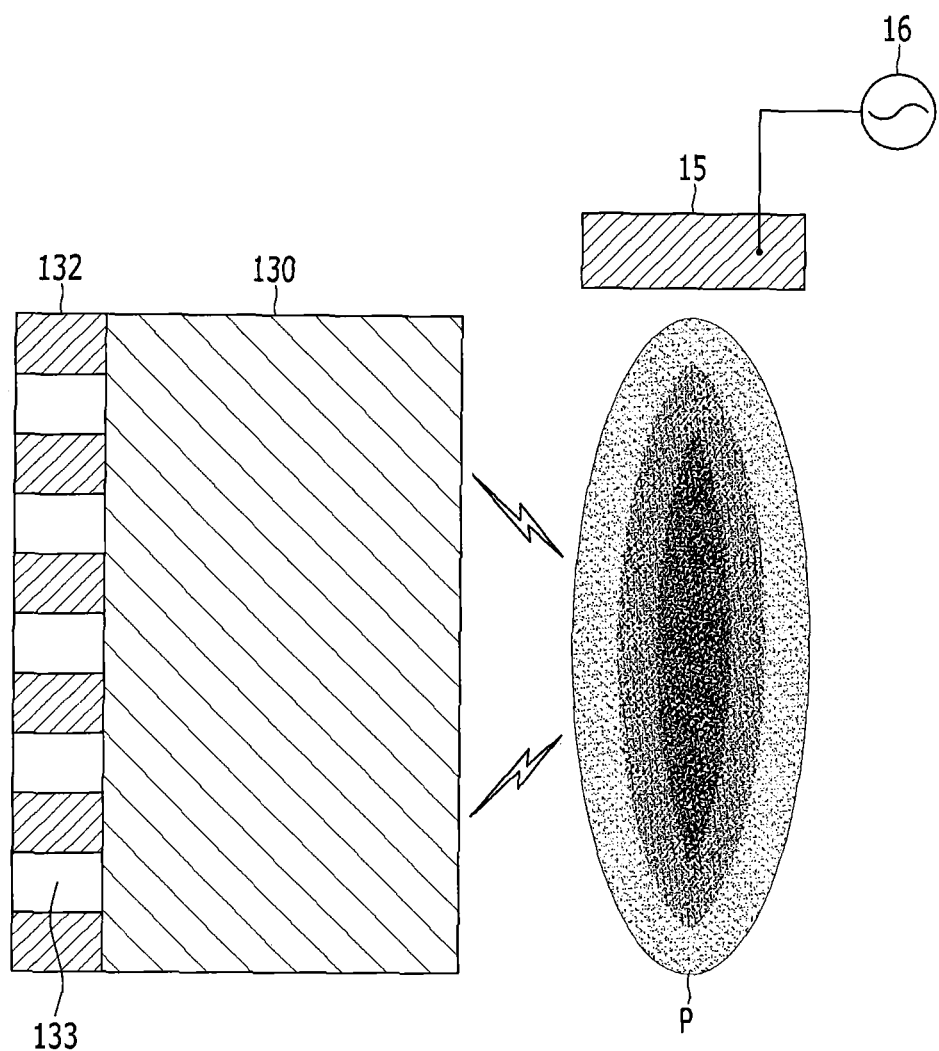
FIG. 10 is a diagram illustrating a vibrator in a monitoring unit in the plasma treatment apparatus of FIG. 9.

FIG. 9 is a schematic cross-sectional view of a plasma treatment apparatus according to further embodiments, and FIG. 10 is a diagram illustrating a vibrator in a monitoring unit in the plasma treatment apparatus of FIG. 9.

Referring to FIG. 9, a monitoring unit 100 may include a transparent window 130. The window 130 may formed of quartz, and may be inserted into and installed in an opening formed on a side wall of a chamber 11. For example, the window 130 may include an end point detecting (EPD) window which allows light generated during an etching process to pass through. An end point of a process may be determined by detecting a change in wavelength of the light generated by the process. In some embodiments, the EPD window may be formed of quartz.

Referring to FIG. 10, one electrode 132 in a pair of electrodes configuring the vibrator may be installed in or on the window 130, and the other electrode may be a head electrode 15 of a head plate 14 (see FIG. 3) to which an RF voltage is applied for generating plasma P. For example, in a case of the etching process, one side of the window 130, that is, a side facing an inner side of the chamber 11, may be exposed to and eroded in the plasma P, and one electrode 132 may be attached to the other side of the window 130, that is, a side facing the outside of the chamber 11. Accordingly, when a voltage is applied to the head electrode 15, a current may be transmitted to one side of the window 130 through the plasma P that is a conductor, and may flow to the other electrode 132 disposed on the other side of the window 130. Accordingly, the window 130 may serve as a vibrator, and as one side of the window 130 exposed to the plasma P is eroded, a frequency of the vibrator will change. In this case, it is enough to install only one electrode in the window 130, and the head electrode 15 of the plasma etching apparatus may be used as an electrode of the vibrator. In this case, it may not be necessary to provide a separate voltage supply means, such as the voltage supply unit 140 (see FIG. 1), to supply a voltage to the vibrator.

In some embodiments, an opening 133 may be formed in one electrode 132 attached to the window 130. As described above, the window 130 may be the EPD window, and in this case, a wavelength of a by-product generated during the etching process will be transmitted through the window 130. Accordingly, the opening 133 may be formed in the electrode 132 attached to the window 130 so as to allow light to pass through. In this case, in order to sufficiently transmit the quantity of light, a plurality of openings may be formed. In other embodiments, the electrode 132 may be a transparent electrode that allows the wavelength of light to pass therethrough. Transparent electrodes are well known in the art.

In other embodiments, one of the pair of electrodes configuring the vibrator including the window 130 may be a stage electrode 13 (see FIG. 3) of a stage 12. That is, the window 130 formed of quartz, the stage electrode 13, and the electrode 132 attached to the window 130 may form the vibrator.

Further, although not illustrated in the drawings, a plurality of window 130 may be arranged on an inner wall of the chamber 11. In this case, it may be possible to monitor a spatial characteristic within the chamber 11 of the plasma treatment process.

A method of fabricating a semiconductor chip by performing a plasma treatment process on a substrate by using the plasma treatment apparatus will now be described. As part of the method of fabricating the semiconductor chip, a process of performing a plasma treatment process on a substrate while monitoring the plasma treatment process by using the plasma treatment apparatus according to some embodiments will be described.

First, a substrate W that is to be plasma treated is positioned within a chamber 11. In this case, the substrate W may have a disk form, and may be fixed or placed onto a stage 12.

Next, plasma is formed within the chamber 11. For example, reaction gas may be supplied from a head plate 14 on the substrate W, and an RF voltage may be applied to a first electrode 15 and a second electrode 13 to form plasma within the chamber 11.

Next, a voltage is applied to a piezoelectric member disposed within the chamber 11. In this case, the piezoelectric member may be exposed to the plasma, and a pair of electrodes is disposed with the piezoelectric member interposed therebetween to provide a vibrator. For example, a first quartz ring 110, a second quartz ring 120, or a window 130 provided within the chamber 11 may provide the vibrator together with the pair of electrodes. In this case, at least one of the pair of electrodes may be inserted into and installed inside the piezoelectric member so as not to be exposed to the plasma. Otherwise, one of the pair of electrodes may be installed in the piezoelectric member, and the other may be a head electrode 15 or a stage electrode 13. In embodiments in which the electrodes are inserted into and installed in the piezoelectric member, the pair of electrodes may be connected to a separate power supply unit. In embodiments in which one of the pair of electrodes providing the vibrator is the head electrode 15 or the stage electrode 13, power applied to the head electrode 15 or the stage electrode 13 may be used as it is without a separate power supply unit. When a voltage is applied to the piezoelectric member as described above, the piezoelectric member vibrates.

When the piezoelectric member vibrates, a frequency vibration of the piezoelectric member is monitored. In this case, it is possible to monitor a plasma treatment process in real time by monitoring the frequency of vibration of the piezoelectric member.

For example, in a case of an etching process, a surface of the piezoelectric member exposed to the plasma is eroded due to the etching process, and a vibration frequency of the piezoelectric member is changed due to erosion of the piezoelectric member. It is possible to detect the amount of erosion of the piezoelectric member by analyzing a change in the frequency of vibration. It is possible to monitor a replacement time of the piezoelectric member, for example, the first quartz ring 110, the second quartz ring 120, or the window 130 formed of quartz, by using the detected amount of erosion of the piezoelectric member. Further, in embodiments in which the vibrator is formed of the first quartz ring 110 or the second quartz ring 120, it is possible to analyze a characteristic change of the etching process for a surrounding region of the border of the substrate W by analyzing a change in the vibration frequency of the vibrator. In general, an etching process may not be uniformly performed in a region surrounding the border of the substrate W. When a characteristic change of the etching process in the region surrounding the border of the substrate W is monitored, it may be possible to more effectively improve the etching process. For example, a characteristic of the etching process for the region surrounding the border of the substrate W may be established as data, and the established data may be utilized when the etching process is improved. Further, in a case where the first quartz ring 110 and the second quartz ring 120 are divided into a plurality of pieces, it is possible to determine spatial uniformity of the etching process by analyzing changes to the vibration frequencies of each piece. The spatial uniformity of the etching process may directly affect a quality of a semiconductor chip, so that it may be possible improve a quality of the semiconductor chip fabricated on the substrate.

It is possible to control the plasma treatment process according to a result of the monitoring of the frequency of the piezoelectric member. That is, the result of monitoring the frequency of the piezoelectric member may be fed back to the plasma treatment process. For example, when it is determined that it is time to replace the piezoelectric member, the plasma treatment process may be interrupted, and the piezoelectric member may be replaced. Further, if it is determined that there is an abnormality in the etching process in the region surrounding the border of the substrate, or if it is determined that there is a problem in spatial uniformity of the etching process, the process may corrected by checking equipment, adjusting process conditions, etc.

As described above, the present disclosure has been described through the limited exemplary embodiments and the drawings, but the present disclosure is not limited thereto, and may be variously corrected and modified within the technical spirit of the present disclosure and an equivalent range of the claims described below by those skilled in the art.

What is claimed is:

1. An apparatus comprising:
a controller that monitors a plasma process chamber;
a piezoelectric member circumferentially surrounding an RF electrode within the plasma process chamber and comprising a surface that is exposed within the plasma process chamber, wherein the piezoelectric member is a piezoelectric material ring with an inner diameter substantially equal to a diameter of the RF electrode;
a first electrode embedded in the piezoelectric member;
a power supply coupled to the first electrode and configured to apply a voltage to the piezoelectric member through the first electrode; wherein
the controller is coupled to the piezoelectric member;
the controller is configured to detect a change in a vibration frequency of the piezoelectric member, and
the vibration frequency is generated based on the voltage being applied to the piezoelectric member by the power supply.

2. The apparatus of claim 1, further comprising:
a second electrode in the plasma process chamber,
wherein the power supply is connected to the first electrode and the second electrode.

3. The apparatus of claim 1, wherein
the piezoelectric member comprises a plurality of piezoelectric members arranged in a ring,
the first electrode comprises a plurality of first electrodes coupled to the plurality of piezoelectric members, and
the monitoring of the plasma process chamber includes detecting a plurality of changes in vibration frequencies of the plurality of piezoelectric members.

4. The apparatus of claim 1, wherein the plasma process chamber comprises a plasma etching chamber, and the vibration frequency of the piezoelectric member changes in response to erosion of the piezoelectric member during a plasma etching process conducted in the plasma etching chamber.

5. The apparatus controller of claim 1, wherein the monitoring unit is configured to monitor a change to a quartz component within the plasma process chamber, and wherein the piezoelectric member comprises quartz.

6. The apparatus of claim 1, wherein
the monitoring of the plasma process chamber includes monitoring a change to a quartz component within the plasma process chamber, and
the piezoelectric member comprises a material other than quartz.

7. A plasma treatment apparatus comprising:
a chamber;
a stage in the chamber, wherein the stage is configured to support a substrate that is to be subjected to a plasma treatment process;
a head plate in the chamber and disposed to face the stage;
a piezoelectric member surrounding the stage or the head plate and having a surface that is exposed within the chamber, wherein the piezoelectric member is a piezoelectric material ring with an inner diameter substantially equal to a diameter of the stage or the head plate;
a pair of electrodes connected to a power supply and configured to apply a voltage to the piezoelectric member, at least one of the pair of electrodes embedded in the piezoelectric member; and a controller configured to monitor the plasma treatment process within the chamber;
the monitoring of the plasma process includes detecting a change in a vibration frequency of the piezoelectric member; and
the vibration frequency is generated based on the voltage being applied to the piezoelectric member by the power supply.

8. The plasma treatment apparatus of claim 7, wherein the piezoelectric member comprises a quartz ring that circumferentially surrounds the stage or the head plate.

9. The plasma treatment apparatus of claim 7, wherein both of the pair of electrodes are embedded within the piezoelectric member.

10. The plasma treatment apparatus of claim 7, wherein
the piezoelectric member comprises a plurality of radially divided pieces, and
the plasma treatment apparatus further comprising a plurality of first electrodes coupled to the radially divided pieces and to the controller.

11. The apparatus of claim 1, wherein the first electrode comprises a first ring-shaped electrode embedded in the piezoelectric material ring.

12. The apparatus of claim 11, further comprising a second ring-shaped electrode embedded in the piezoelectric material ring concentric with the first ring-shaped electrode and connected to the power supply.

13. The plasma treatment apparatus of claim 7, wherein at least one of the pair of electrodes comprises a ring-shaped electrode embedded in the piezoelectric material ring.

14. The plasma treatment apparatus of claim 13, wherein the pair of electrodes comprises concentric first and second ring-shaped electrodes embedded in the piezoelectric material ring.

15. The plasma treatment apparatus of claim 8, wherein at least one of the pair of electrodes comprises a ring-shaped electrode embedded in the quartz ring.

16. The plasma treatment apparatus of claim 15, wherein the pair of electrodes comprises concentric first and second ring-shaped electrodes embedded in the quartz ring.

\* \* \* \* \*